United States Patent [19]
Mac Lauchlan et al.

[11] Patent Number: 6,125,703
[45] Date of Patent: Oct. 3, 2000

[54] DETECTION OF CORROSION FATIGUE IN BOILER TUBES USING A SPIKE EMAT PULSER

[75] Inventors: Daniel T. Mac Lauchlan; Paul J. Latimer, both of Lynchburg, Va.

[73] Assignee: McDermott Technology, Inc., New Orleans, La.

[21] Appl. No.: 09/105,514

[22] Filed: Jun. 26, 1998

[51] Int. Cl.[7] .................................................. G01N 29/04
[52] U.S. Cl. .............................................. 73/592; 73/598
[58] Field of Search ............................. 73/592, 598, 599, 73/600, 622

[56] References Cited

U.S. PATENT DOCUMENTS

| | | | |
|---|---|---|---|
| 4,184,374 | 1/1980 | Thompson et al. | 73/640 |
| 4,289,030 | 9/1981 | Alers et al. | 73/588 |
| 4,295,214 | 10/1981 | Thompson | 367/140 |
| 4,466,287 | 8/1984 | Repplinger et al. | 73/643 |
| 5,526,691 | 6/1996 | Latimer et al. | 73/592 |
| 5,677,489 | 10/1997 | Spillman, Jr. | 73/598 |
| 5,714,688 | 2/1998 | Buttram et al. | 73/597 |

*Primary Examiner*—Max Noori
*Attorney, Agent, or Firm*—R. J. Edwards; Eric Marich

[57] ABSTRACT

A method of detecting damage in a ferromagnetic workpiece such as a boiler tube positions a pair of EMAT coils adjacent to the workpiece at a non-zero angle with respect to one another. A spike pulse is applied to one of the EMAT coils for generating a horizontally polarized shear wave in the workpiece which is capable of being reflected by a flaw, and the amplitude of a reflected wave from any flaw is received at the other EMAT coil and analyzed and compared to a predetermined percent of an amplitude of a calibration standard flaw to establish the presence of the flaw.

11 Claims, 2 Drawing Sheets

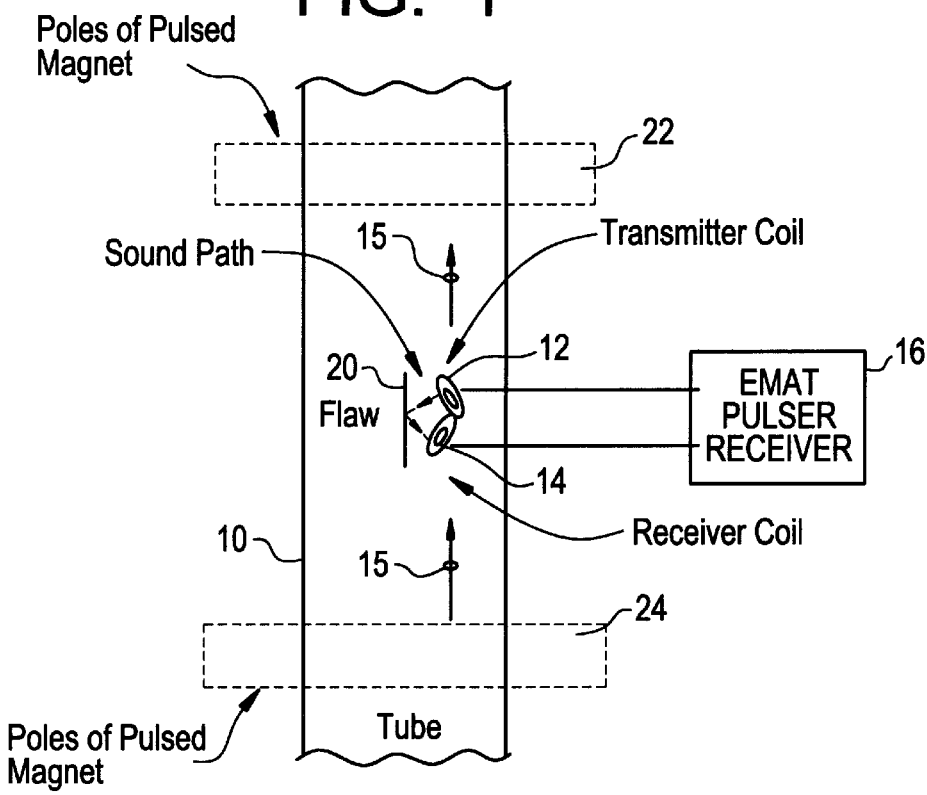
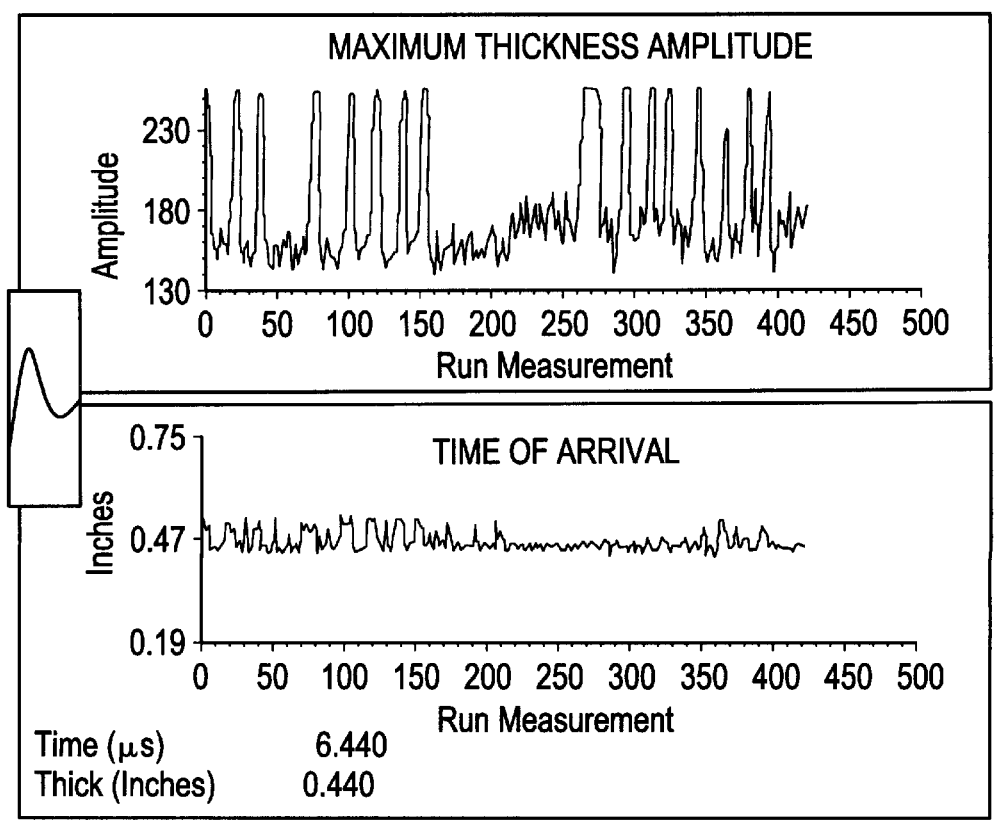

DETECTION OF CORROSION FATIGUE IN BOILER TUBES USING A SPIKE EMAT PULSER

FIELD AND BACKGROUND OF THE INVENTION

The present invention relates generally to nondestructive examination (NDE) techniques used to inspect workpieces for flaws. More particularly, the present invention is drawn to a new and useful method for detecting corrosion fatigue cracks or other flaws in boiler tubes using Electromagnetic Acoustic Transducers (EMATs). The method according to the present invention is particularly suited to the task of detecting flaws in a ferromagnetic component or workpiece such as a boiler tube or a membrane wall tube panel comprised of boiler tubes, even those in close proximity to a probe assembly housing the EMATs.

Corrosion fatigue is a serious failure mechanism for boiler tubes in fossil utility boilers. Mechanical constraints or stress and corrosion work together to produce cracking that is typically oriented axially to the tube axis. This type of damage is usually found close to weld attachments such as buckstay welds. In the past, it has been particularly difficult to locate this type of damage due to the complex geometry of the usual membrane boiler tube panels. Solving the problem of detection of corrosion fatigue is ranked near the top in priorities by the Electric Power Research Institute (EPRI).

As noted, stresses are typically found adjacent the buckstay welds on the casing (cold) side of the furnace wall in a fossil utility boiler. The cracking mechanism may occur in other areas in the boiler; however, the furnace wall is particularly important because the resulting tube failures can lead to a continuing sequence of forced outages. Detection is difficult with ultrasonic techniques (UT) because of the complex geometry of membrane panels. Radiography testing (RT) has been used in the past; however, it is no longer used because of the safety hazard.

U.S. Pat. No. 5,526,691 to Latimer et al. addresses the need for the detection of corrosion fatigue in boiler tubes. The technique of the '691 patent uses a tone-burst pulser to produce horizontally polarized shear waves (SH waves) to propagate past the membrane of a tube panel and detect damage on the casing (cold) side of the furnace wall while the inspection is performed from the fireside. Advantages of that approach include the fact that the casing does not have to be removed, access is easier from the furnace side with stationary or floating scaffolding, and detection of corrosion fatigue cracks from the areas with welded attachments (such as buckstay welds) is more easily accomplished.

SUMMARY OF THE INVENTION

The present invention provides an EMAT sensor inspection method that is very efficient at detecting corrosion fatigue cracks because it is used where corrosion fatigue occurs with a high probability. In contrast to the tone burst technique employed in U.S. Pat. No. 5,526,691 to Latimer et al., the "spike" pulse technique according to the present invention (as described infra) can employ an EMAT sensor in situations where the sensor and the flaw are on the same side of the workpiece. Another advantage to using the spike pulse technique of the present invention is the fact that range of inspection of the EMAT coils may be extended by slightly changing the angle of the EMAT sensor with respect to the workpiece.

The method according to the present invention is not limited to the task of detecting only corrosion fatigue cracks; it will detect cracking or the presence of flaws caused by other mechanisms. This is an advantage because it can be used to detect any cracks in an axial orientation and thus prevent a forced outage due to a tube failure in the unit.

Accordingly, one aspect of the present invention is drawn to a method for detecting a flaw in a ferromagnetic workpiece, comprising the steps of: positioning a pair of EMAT coils adjacent to an outer surface of the workpiece at a non-zero angle with respect to one another; applying a spike pulse to one of the EMAT coils for magnetostrictively generating a shear horizontal polarized wave in the workpiece and which is capable of being reflected by a flaw in the workpiece; receiving a reflected wave from a flaw in the workpiece at the other EMAT coil; and analyzing the received reflected wave and comparing an amplitude thereof to an amplitude of a reflected wave produced by a known calibration standard flaw and producing an indication that a flaw has been detected in the workpiece when the amplitude of the received reflected wave exceeds a predetermined percent of the amplitude of the reflected wave produced by the known calibration standard flaw.

Another aspect of the present invention is drawn to a method of detecting corrosion fatigue or other types of flaws in a ferromagnetic workpiece, particularly a boiler tube, which is reliable, rapid, and economical.

The various features of novelty which characterize the invention are pointed out with particularity in the claims annexed to and forming a part of this disclosure. For a better understanding of the invention, its operating advantages and specific benefits attained by its uses, reference is made to the accompanying drawings and descriptive matter in which the preferred embodiments of the invention are illustrated.

BRIEF DESCRIPTION OF THE DRAWINGS

In the drawings:

FIG. 1—is a schematic representation of the probe system used to practice the present invention as applied to a boiler tube;

FIG. 2—is an illustration of a display used for practicing the present invention;

DESCRIPTION OF THE PREFERRED EMBODIMENTS

Figure 3:
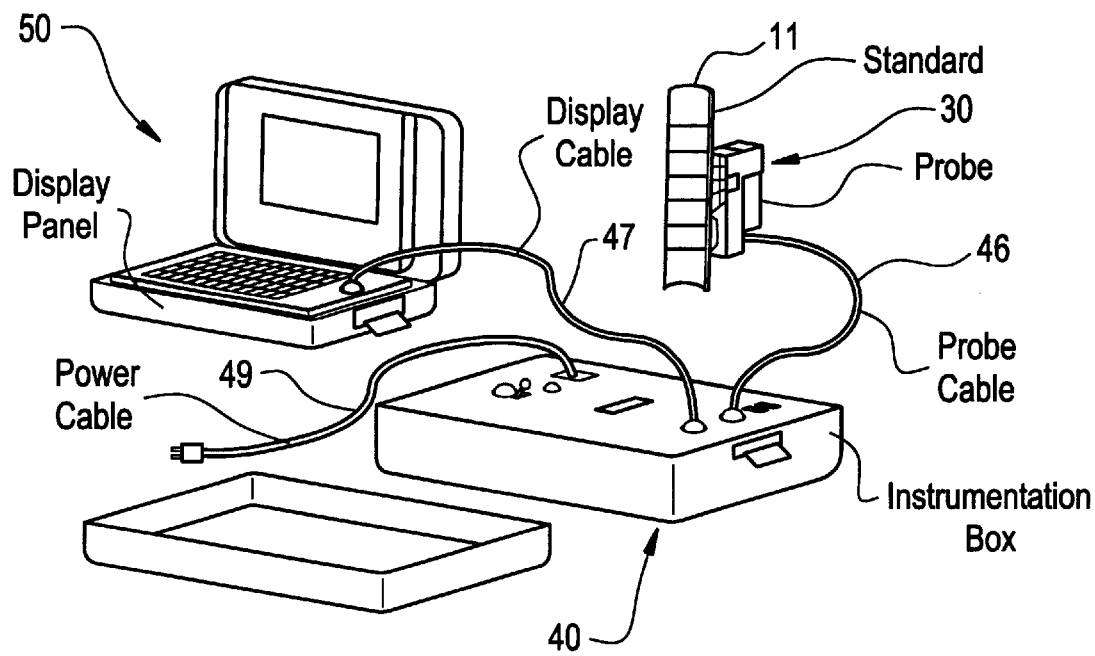
FIG. 3—is a perspective view of the system used in accordance with the present invention.

U.S. Pat. No. 5,526,691 to Latimer et al. is hereby incorporated by reference as though fully set forth herein to disclose the various techniques for setting up and using EMATs in a boiler environment.

The principles behind the present invention will be understood with reference to the drawings accompanying and forming a part of this disclosure, wherein like reference numerals designate the same or functionally similar elements throughout the several drawings. Referring to FIG. 1 in particular, the method according to the present invention uses two rectangular EMAT transmitting and receiving coils 12, 14, respectively, to inspect a ferromagnetic workpiece or tube 10. EMAT coils 12, 14 are positioned adjacent to the workpiece or tube 10, and are preferably oriented either at a right angle with respect to each other or at some convenient angle preferably within a range of approximately 30° to approximately 150°. A spike EMAT pulser/receiver 16 is used to produce a broadband pulse which is transmitted from EMAT transmitter coil 12 and which is reflected by a flaw 20 in the workpiece 10 and then received by the EMAT receiver coil 14 and relayed to the spike EMAT pulser/receiver 16. The presence of the flaw 20 in workpiece 10 is indicated by analyzing the received reflected wave and comparing an amplitude thereof to an amplitude of a reflected wave produced by a known calibration standard flaw. An indication that a flaw 20 has been detected in the workpiece 10 is provided when the amplitude of the received reflected wave exceeds a predetermined percent of the amplitude of the reflected wave produced by the known calibration standard flaw. Typically, this can be accomplished by providing the indication on a computer screen or equivalent device that is similar to most ultrasonic rectified displays (A-scan). If there is no flaw 20 present to reflect the wave back to the receiver coil 14, then there is no signal on the screen. The user determines the value of the predetermined percent based upon what size flaws 20 are of interest, and the value of the percent can be less than, equal to, or greater than 100 percent.

In practice, to inspect boiler tubes 10 for the presence of corrosion fatigue cracks (which tend to run axially with the tubes and tend to occur more often on the casting side thereof) with the method of the present invention, any insulation covering the tubes 10 is removed from the casing side of the tubes 10. A probe 30 (FIGS. 3, 4) carrying the EMAT transmitting and receiving coils 12, 14 is scanned close to the welding attachments to the tubes 10 where cracking is known to occur with a high probability. The amplitude of any reflected signals is compared with the predetermined percent of the amplitude from, for example, a 0.050" deep notch in a known calibration standard 11 in order to obtain sizing information about any flaws 20 which might be encountered. Received reflected signals with amplitudes greater than the predetermined percent of the amplitude obtained from such a known calibration standard 11 would be interpreted or indicated by the method as flaws 20.

The method of the present invention can be used to detect flaws 20 at the crown of the tubes 10, at the membrane welds interconnecting such tubes 10 to form a gas-tight enclosure, or at other structures connected thereto. These are the areas where failures are most likely to occur. The use of a pitch-catch technique in the method of the present invention avoids the problems of propagating sound past the membrane welds in the complex geometry of these membrane coiler tube panels.

The angle between the two EMAT coils 12, 14 can be increased to allow the method according to the present invention to be used on the entire range of boiler tube 10 sizes.

Inspection with the EMAT probe of the invention is performed on the side of the furnace tubes where damage is expected. The pitch-catch EMAT coils 12, 14 are located between poles 22, 24 of the magnet. The signal from the EMAT transmitter coil 12 propagates as shown in FIG. 1. Without a flaw 20, there is no received signal. However, if a flaw 20 is present, sound is reflected into the EMAT receiver coil 14 and an indication is observed on the instrument display panel 50. FIG. 2 illustrates a typical indication. The indication is from an EDM notch with dimensions 1" (25.4 mm) long×0.050" (1.27 mm) deep on the ID of the crown of the tube 10 in a membrane panel with tubes 10 having a diameter of 1.25" (31.75 mm) and a wall thickness of 0.188" (4.8 mm). In FIG. 2, the EDM notch has been scanned a number of times to determine the repeatability of the measurement. Note that the signal-to-noise ratio displayed by this simulated defect is very good.

With the configuration tested, one scan will detect cracks or flaws 20 on the crown of the tube 10. Additional scans can detect cracks or flaws 20 along the two membrane welds on either side of the tube 10. This technique proved that it is possible to use the EMAT probe 30 for the detection of corrosion fatigue cracks. With its greater scanning speeds, EMATs permit inspection of the high risk areas in a practical time period.

The EMAT probe 30 used in the method of the present invention relies upon the presence of magnetostriction within a distance of one electromagnetic skin depth from the surface of a ferromagnetic conductor. The system configuration of the invention shown in FIG. 3 comprises a hand-held EMAT probe 30, instrumentation box 40, display panel 50, cables 46, 47 and 49, and the known calibration standard 11. The compact design allows for a one or two-man operation. All components are designed for protection from dust, dirt, ash and liquids.

Figure 4:
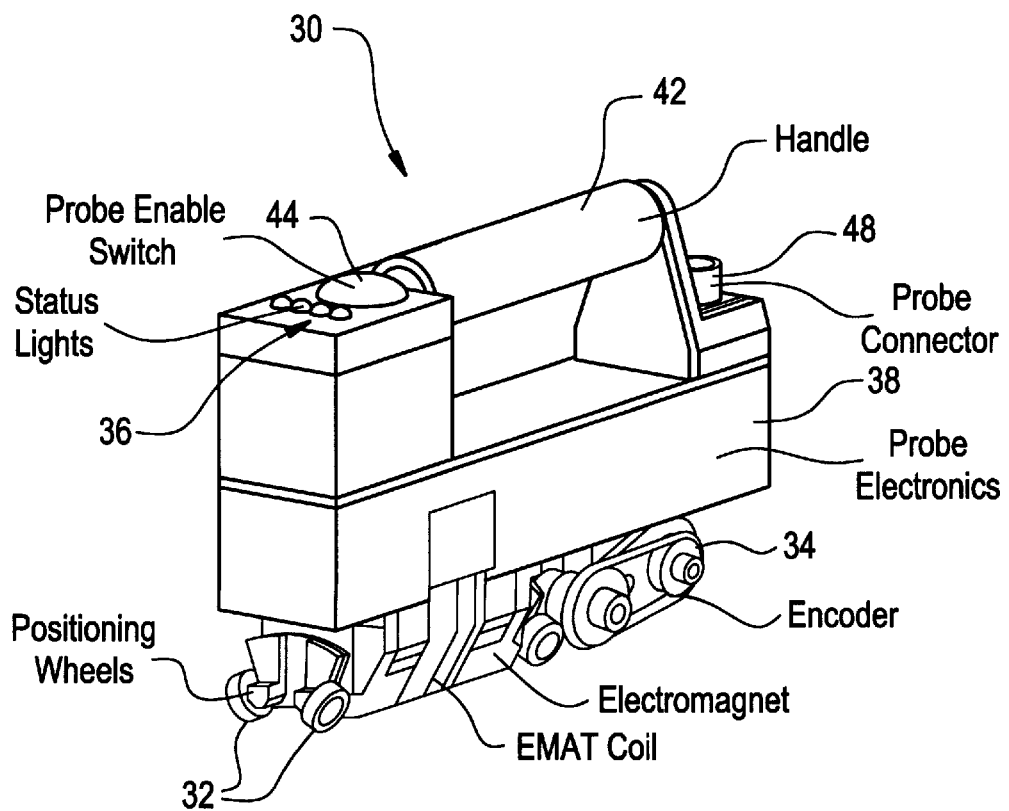
FIG. 4—is a perspective view of a hand held probe for use in practicing the method of the present invention.

As illustrated in FIG. 4, the probe 30 is a rugged, hand-held device weighing less than four pounds (1.8 kg), and is positioned and moved in contact with the tube 10 under inspection. The probe 30 is constructed from corrosion resistant materials and sealed from dust and dirt. The ergonomic design minimizes fatigue. Positioning wheels 32 provide smooth operation during scanning and assure proper alignment and sensor spacing. The positioning wheels are adjustable for the full range of tube 10 diameters. A single-axis encoder 34 is included which enables a computer in the instrumentation box 40 to derive axial tube elevation information for recording the measurements. A minimum positional resolution of 0.005" (0.127 mm) is supported along the length of a boiler tube 10. Status lights 36 on the probe enable the operator to easily determine status and feedback of inspection conditions including: probe enables, scan speed fault, and defect detected indicator.

Probe electronics are provided in a probe housing 38, and a handle 42 is used to carry the probe 30. An enable switch 44 is within easy reach of the handle 42. Cable 46 connects instrumentation box 40 to probe connector 48.

The instrumentation box 40 is sized to fit through boiler manways and weighs less than 40 pounds (18.1 kg). The components are designed to operate in temperatures up to 120° F. (49° C.). A compact, industrial, Pentium® or equivalent personal computer, mounted inside the instrumentation box 40, controls the inspection process and is used to collect, analyze, display and store the inspection results. Communication ports for a printer and serial device are included.

The software operates in a Windows™-based environment with an easy-to-use menu scheme. All software functions are selected through keyboard entry. The software includes setup, scan, and playback modules. Multiple setup configurations can be stored and retrieved. The setup module provides readout display of control values and real-time readout display of time-of-flight, and amplitude measurements. Prior to inspection, a simple entry form provides for input of scan information. The scan information is displayed and recorded with the corresponding inspection data. The scan module provides the ability to enter scan information, perform an inspection scan, display and record the results. Both position-based and time-based triggering functions are available. The scan module permits entry of codes, descriptions and distances skipped for obstructions that block scanning. The entered information is saved with the inspection record. Data is exported in a format that can be easily imported to most data analysis programs such as an EPRI Boiler Maintenance Workstation.

The display panel 50 is a portable user interface for the probe 30. The display panel 50 includes an active matrix, flat panel color video display and keyboard, connected by a single cable 47 to the instrumentation box. The display panel, weighing less than 15 pounds (6.8 kg), includes an attached strap to enable hands-free support of the unit during operation.

A standard power cable 49 with a 3 prong connector is supplied with the probe 30. A ground fault interrupt circuit is implemented on the electrical power input which requires an external 115 VAC power source.

The known calibration standard 11 is a section of representative boiler tubing 10 which has been machined to contain calibration standards of known dimensions.

Tests were made in the laboratory using a membrane boiler tube panel. The outside diameter (OD) of the tubes was 1.25" with a wall thickness of 0.188". The notch representing a flaw 20 used for detection was 0.9" long and 0.050" deep. The flaw 20 was scanned several times in order to demonstrate that the measurement was repeatable. The presence of the flaw 20 was indicated by the increase in amplitude in the upper trace on a display screen.

The duration of the spike pulse is preferably approximately 0.7 microseconds, but a spike pulse in a range of approximately 0.1 microseconds to approximately 10 microseconds can be used in other applications.

To detect corrosion fatigue, the method of the present invention positions the two EMAT coils 12, 14 (preferably rectangular in configuration) which are oriented at some non-zero angle with respect to one another, in a range of approximately 30° to approximately 150° and uses them to send and receive such shear horizontal polarized waves in the workpiece 10. Shear horizontal waves are most efficiently generated when the EMAT coil makes an angle of 40° to 60° with respect to an axis 15 (FIG. 1) of the applied magnetic field. However, useable signals can be obtained when the coils 12, 14 form an angle of about 15° to about 75° with respect to the axis 15 of the applied magnetic field. Selection of the proper angle of the EMAT coils 12, 14 allows the shear horizontal waves to be efficiently produced and the main bang signal is reduced, allowing close proximity flaw detection.

The preferred arrangement of the coils 12, 14 is thus to have them at an angle of 90° with respect to each other, or 45° with respect to the axis 15 of the magnetic field created between the poles of the pulses magnet 22, 24, and which axis 15 runs substantially along the axis of the tube 10 in the area being interrogated by the EMAT probe 30. The EMAT spike pulser/receiver 16 is used to produce a short spike pulse instead of a tone burst pulser that is more commonly used to produce a tone burst consisting of several cycles of ultrasound. The principle of operation is to produce a pulse that is reflected by the axial flaw and received by the EMAT receiver coil. The presence of the flaw 20 is demonstrated by an increased amplitude which is greater than the amplitude of a signal produced from a known calibration standard flaw on the computer screen or device that is similar to most ultrasonic rectified displays (A-scan) as noted. If there is no flaw present to bounce the ultrasound back to the receiver coil, then there is no signal on the screen. In practice, the probe 30 is scanned close to the welding attachments or structures where corrosion fatigue is known to occur with a high probability. An EMAT spike pulser is used because of the close proximity of the EMAT coils to the flaw. In this technique, the EMAT sensor is on the same side of the tube 10 as the crack or flaw 20. Therefore, the initial pulse excitation (main bang), must not extend very far in time and the time resolution must be good in order to detect the flaw close to the sensor. These characteristics are met by the EMAT spike pulser/receiver 16. The more commonly used tone burst sensor would produce a main bang that would extend too far in time to detect flaws at close proximity.

While specific embodiment of the invention have been shown and described in detail to illustrate the application of the principles of the invention, it will be understood that the invention may be embodied otherwise without departing from such principles.

We claim:

1. A method for detecting damage in a ferromagnetic workpiece, comprising the steps of:

positioning a pair of EMAT coils adjacent to an outer surface of the workpiece at a non-zero angle with respect to one another;

applying a spike pulse to one of the EMAT coils for a period of time which is less than the time required to generate a toneburst signal in the one of the EMAT coils in order to magnetostrictively generate a shear horizontal polarized wave in the workpiece, wherein the shear wave is capable of being reflected by a flaw in the workpiece;

receiving a reflected wave from a flaw in the workpiece at the other EMAT coil; and analyzing the received reflected wave and comparing an amplitude thereof to an amplitude of a reflected wave produced by a known calibration standard flaw and producing an indication that a flaw has been detected in the workpiece when the amplitude of the received reflected wave exceeds a predetermined percent of the amplitude of the reflected wave produced by the known calibration standard flaw.

2. The method according to claim 1 comprising the step of positioning the EMAT coils at a non-zero angle with respect to one another of approximately 30° to approximately 150°.

3. The method according to claim 1 comprising the step of positioning the EMAT coils at a non-zero angle with respect to one another of approximately 80° to approximately 100°.

4. The method according to claim 1 comprising the step of positioning the EMAT coils at a non-zero angle with respect to one another of approximately 45° to approximately 90°.

5. The method according to claim 1 comprising the step of positioning the pair of EMAT coils on an outer surface of a boiler tube to detect the presence of a flaw within one of the boiler tube and an attached structure.

6. The method according to claim 1 comprising the step of positioning the pair of EMAT coils on an outer surface of a casing side of a boiler tube to detect the presence of a flaw within one of the boiler tube and an attached structure.

7. The method according to claim 1, wherein the period of time in the applying the spike pulse step is between 0.1 and 10 microseconds.

8. The method according to claim 1, wherein the period of time in the applying the spike pulse step is approximately 0.7 microseconds.

9. The method according to claim 1 comprising the steps of displaying the reflected wave from the flaw and producing a visible indication that a flaw has been detected.

10. A method for detecting corrosion fatigue damage in a ferromagnetic boiler tube, comprising the steps of:

positioning a pair of EMAT coils adjacent to an outer surface of the ferromagnetic boiler tube at a non-zero angle with respect to one another;

applying a spike pulse to one of the EMAT coils for a period of time which is less than the time required to generate a toneburst signal in the one of the EMAT coils in order to magnetostrictively generate a shear horizontal polarized wave in the ferromagnetic boiler tube, wherein the shear wave is capable of being reflected by a corrosion fatigue flaw therein;

receiving a reflected wave from a corrosion fatigue flaw in the ferromagnetic boiler tube at the other EMAT coil; and analyzing the received reflected wave and comparing an amplitude thereof to an amplitude of a reflected wave produced by a known calibration standard flaw and producing an indication that a corrosion fatigue flaw has been detected in the ferromagnetic boiler tube when the amplitude of the received reflected wave exceeds a predetermined percent of the amplitude of the reflected wave produced by the known calibration standard flaw.

11. A method for detecting a flaw in a ferromagnetic boiler tube, comprising the steps of:

positioning a pair of EMAT coils adjacent to an outer surface of the ferromagnetic boiler tube at a non-zero angle with respect to one another;

applying a spike pulse to one of the EMAT coils for a period of time which is less than the time required to generate a toneburst signal in the one of the EMAT coils in order to magnetostrictively generate a shear horizontal polarized wave in the ferromagnetic boiler tube, wherein the shear wave is capable of being reflected by a flaw therein;

receiving a reflected wave from a flaw in the ferromagnetic boiler tube at the other EMAT coil; and analyzing the received reflected wave and comparing an amplitude thereof to an amplitude of a reflected wave produced by a known calibration standard flaw and producing an indication that a flaw has been detected in the ferromagnetic boiler tube when the amplitude of the received reflected wave exceeds a predetermined percent of the amplitude of the reflected wave produced by the known calibration standard flaw.

* * * * *